United States Patent [19]

Wheeldon et al.

[11] Patent Number: 4,670,007
[45] Date of Patent: Jun. 2, 1987

[54] FLUID FLOW CONTROL PROCESS AND APPARATUS

[75] Inventors: Peter G. Wheeldon, Guildford; John Kent, Nr. Petworth, both of England

[73] Assignee: Peritronic Medical Industries plc, London, England

[21] Appl. No.: 580,058

[22] Filed: Feb. 14, 1984

Related U.S. Application Data

[63] Continuation-in-part of Ser. No. 519,349, Aug. 1, 1983, abandoned.

[30] Foreign Application Priority Data

Aug. 3, 1982 [GB] United Kingdom ............... 8222389

[51] Int. Cl.⁴ .............................................. A61M 5/00
[52] U.S. Cl. ...................................... 604/65; 604/67; 128/DIG. 13
[58] Field of Search ............... 128/DIG. 12, DIG. 13; 604/49, 50, 65, 67, 151, 153, 246

[56] References Cited

U.S. PATENT DOCUMENTS

| | | | |
|---|---|---|---|
| 3,855,458 | 2/1974 | Motter et al. | 235/151 |
| 4,137,915 | 2/1979 | Kamen | 604/65 |
| 4,210,138 | 7/1980 | Jess et al. | 604/67 |
| 4,457,750 | 7/1984 | Hill | 128/DIG. 13 |
| 4,457,751 | 7/1984 | Rodler | 604/67 |
| 4,464,172 | 8/1984 | Lichtenstein | 604/65 |

FOREIGN PATENT DOCUMENTS

| | | |
|---|---|---|
| 600892 | 7/1978 | Fed. Rep. of Germany. |
| WO82/03554 | 10/1982 | PCT Int'l Appl. . |
| 1117278 | 6/1968 | United Kingdom . |
| 2054200A | 7/1979 | United Kingdom . |
| 2069063A | 2/1980 | United Kingdom . |

*Primary Examiner*—Edward M. Coven
*Assistant Examiner*—David Shay
*Attorney, Agent, or Firm*—Biebel, French & Nauman

[57] ABSTRACT

The invention is concerned with controlling fluid delivery by a fluid dispensing system in which fluid is dispensed from a container, through a delivery tube, under the control of a flow controller or peristaltic pump and, particularly, with the control of the rate of fluid delivery to a patient by an intravenous infusion system utilizing a standard administration set. The control apparatus continually monitors the weight loss of the fluid container, as fluid is dispensed, and produced data identifying the actual fluid delivery rate. It compares this data with a signal identifying the selected delivery rate and provides for adjustment of the flow controller or pump so as to conform the actual delivery rate to the selected rate. Because weight signals for computing the actual delivery rate are not immediately available upon initiation of a dispensing operation, the selected rate signal is initially processed by the apparatus to produce data for setting the flow controller or pump speed to a value nominally corresponding to the selected delivery rate so that the the actual delivery rate is controlled as accurately as possible from the start of the dispensing operation.

7 Claims, 3 Drawing Figures

FLUID FLOW CONTROL PROCESS AND APPARATUS

CROSS-REFERENCE TO RELATED APPLICATION

This application is a continuation-in-part of our application Ser. No. 519,349 filed Aug. 1, 1983, assigned to the same assignee as the present application, and now abandoned.

BACKGROUND OF THE INVENTION

The present invention relates to a flow control process and apparatus for fluid delivery systems in which fluid is dispensed from a fluid reservoir or container under the control of a pump. More particularly, the invention relates to controlling the rate of delivery of fluid administered to a patient by an intravenous infusion system utilising a standard administration set.

Many applications in the field of intravenous infusion therapy require precise control of the accuracy in administering both the total volume to be infused and the rate at which infusion takes place. Such precise infusions are usually undertaken with the aid of devices commonly referred to as "volumetric infusion pumps" wherein accurate delivery is achieved by means of precisely made sections of tubing or cylinders which contain a known volume of fluid and from which this fluid is discharged at a known rate, thereby accurately dispensing specific volumes of fluid at preset delivery rates.

Whilst satisfactory in operation, the main disadvantage of such infusion pumps is the need for special tubes or cylinders which, once used, must be discarded for reasons of sterility. Compared, therefore, with a conventional gravity infusion apparatus, which employs a cheap standard administration set, the cost per infusion using a volumetric infusion pump is relatively expensive. Furthermore, the disposables inventory at a medical establishment must be increased to include special items required by these volumetric pumps.

Normal gravity infusion, although low in cost owing to the use of mass-produced disposable standard administration sets, is totally unsuitable for precisely controlled infusions because the accuracy of delivery cannot be practically controlled even with the aid of a conventional flow controller. Similarly, the "drip-rate" type of device, over which control is maintained by counting drops, is capable of providing an accurate drop delivery rate, often with standard administration sets, but cannot provide volumetric accuracy owing to the wide variation in drop sizes.

For medical purposes, it is unacceptable to monitor flow-rate by means of a metering device introduced into a fluid stream being intravenously administered because this violates the required sterile barrier. Measurement must therefore be external to this barrier. Equally, measurement by passing fluid into a graduated container is unacceptably cumbersome and, without the addition of expensive equipment, precludes automatic calibration.

One type of pump which does not violate the required sterile barrier is a peristaltic pump. The latter can be arranged to deliver fluid using a standard administration set and may be provided with controls which regulate the speed of the motor and, hence, the pumping rate during operation of the pump. Adjustment of the controls to vary the speed of the motor changes the rate of fluid delivery and the pump may incorporate a visual display to indicate to the operator the rate of fluid flow for a selected position of the controls. The pump may also include a facility for adjusting the display to conform to the actual pumping performance of the tube on which it is operating by measurement of a known volume in a known time. This synchronising of actual performance with displayed performance is known as calibration.

Once calibrated, it would be reasonable to expect the actual delivery rate, over the speed range of the motor, when operating on other administration sets of the same type to comply with that selected by the controls and indicated by the display and, within certain limits, this is normally the case. However, variations in the delivery performance of tubing of the type used on standard administration sets are such that repeatability of calibrated performance on different samples of the same tube and in different environments is insufficient to maintain volumetric accuracy of the delivery for precise infusion applications, as referred to above. Moreover, the performance of tubing used in administration sets supplied from different sources can vary markedly. There are many reasons why the performance of tubing varies when used for pumping applications, but there is no need to expand on these in the present specification. Suffice it to say that unacceptable variations occur and these have hitherto precluded the use of peristaltic pumps for infusions requiring precise volumetric delivery, even when calibrated for the type of tube in actual use.

Variations in tubing performance can largely be eliminated if calibration is carried out directly on the tubing to be used for each infusion since, in this way, both actual and selected fluid delivery can be synchronised with accuracy at the outset of the infusion. However, this approach is tedious and time consuming and is still subject to error because the delivery capacity of the tubing can alter during infusion for various mechanical and environmental reasons.

Having regard to the foregoing, it will be apparent that apparatus in which accurate volumetric delivery can be achieved with standard administration sets would be of considerable advantage in reducing the cost per infusion and alleviating the need for high-cost special disposable items in the inventory of medical establishments.

Several arrangements have been proposed for achieving accurate volumetric delivery with intravenous administration systems, some utilising standard administration sets. Examples of such systems are described in patent specifications Nos. CH-A-600892, GB-A-2054200 and WO-A-82/03554. Basically, all these systems monitor the changing weight of a fluid container or bag as fluid is dispensed and produce weight signals corresponding to the loss in weight. These weight signals are compared with a signal identifying a user selected delivery rate and the resulting signal is used to adjust a flow controller or pump so that the actual delivery rate approaches or corresponds to the selected rate.

Other patent specifications of background interest with regard to the control of fluid delivery rates are GB-A-No. 1117278, U.S. Pat. No. 3,855,458 and GB-A-No. 2069063.

The hitherto known systems which monitor weight loss in order to achieve control of fluid delivery rate do not exercise control over the delivery rate until some interval of time after the start of a dispensing operation when the first weight signal is produced corresponding to the first weight increment loss of the fluid container. Furthermore, they are unlikely to maintain delivery rates continuously constant and avoid fluctuations, as the flow control devices employed are generally actuated on an "open-and-shut" or "on-off" basis. Hence, the known systems suffer from a lack of precision in the control of fluid delivery rate at subsequent stages in a dispensing operation, and they exercise no control of the delivery rate upon start of the operation. This lack of control may not be important for an intravenous feeding system but it is a problem in drug infusion and other administration systems where fluid is administered to a patient at low infusion rates. In these circumstances, for example, an interval of several or more minutes may occur before an acceptable weight signal is produced for comparison with the selected delivery rate signal and the weighing system commences to exercise control of the delivery rate.

In an apparent attempt to alleviate the above problem, WO-A-No. 82/03554 describes a fluid flow control system in which weight loss control circuitry of the type described is combined with drop-rate control circuitry. The combination is said to provide better instantaneous control of the fluid flow. However, such an arrangement must suffer from the same problem, referred to above, as conventional drop rate devices and cannot provide accurate delivery rates owing to the wide variation in drop sizes.

SUMMARY OF THE INVENTION

It is an object of the present invention to provide a fluid flow control process and apparatus which are adapted accurately to dispense fluid, at a selected delivery rate, from a fluid container through a delivery tube without requiring access to the fluid for monitoring purposes. Another object is to provide a fluid flow control process and apparatus for an intravenous infusion system utilising a standard administration set, which alleviate the problems in accuracy and constancy experienced with hitherto known systems of this type. Yet another object is to provide such a process and apparatus which are adapted accurately to dispense fluid at the selected delivery rate throughout a complete dispensing operation.

Hence, the invention is directed to controlling flow in a fluid dispensing system in which fluid is dispensed from a fluid container under the control of a peristaltic pump. The control apparatus includes selection means for selecting the required delivery rate and producing a signal identifying the selected flow rate, a weight sensing device for monitoring the weight of the fluid container and its contents and producing weight signals corresponding to the loss in weight as fluid is dispensed from the container, regulating means for adjusting the speed of the pump motor, and data processing means which processes the weight signals with respect to time and produces data identifying the actual delivery rate, and which is also arranged to compare the actual delivery rate data with the selected delivery rate signal and to control the regulating means, thereby to adjust the speed of the pump motor so that the actual delivery rate approaches or corresponds to the selected rate. According to the invention, the data processing means stores the selected delivery rate signal upon initiation of a dispensing operation and produces control data identifying the setting of the speed of the pump motor nominally corresponding to the selected delivery rate and supplies said control data to the regulating means so that the delivery rate is controlled from the start of the dispensing operation.

The measurement of the weight loss of a fluid container is a simple method of monitoring the flow of fluid dispensed from the container without violating the sterile barrier requirement for medical applications. The changes in weight of the container, with suitable corrections for fluid density, when appropriate, gives a direct indication of the volume of fluid delivered and the relationship of these weight changes to time determines the actual delivery rate. Therefore, regular monitoring of the weight of the container enables a check to be maintained on the actual flow conditions and, by means of a return loop to the pump drive system, this data is used to regulate the actual performance of the system such that it corresponds to the selected delivery rate.

The present invention is particularly designed for controlling an intravenous infusion system utilising a peristaltic pump and a standard administration set for delivery of fluid to a patient and enables such a system accurately and uniformly to perform infusions in accordance with a selected delivery rate.

In one preferred embodiment, the peristaltic pump is driven by a stepping motor and the regulating means comprises an adjustable pulse counter for supplying drive pulses to the stepping motor at a variable pulse rate. The data processing means is arranged to control the setting of the counter and thereby adjust the speed of the pump motor and, hence, the delivery rate.

In order to control volume flow within acceptable limits, the weighing device should be of high resolution and repeatability. Various load cells and transducers operating on established principles, such as strain gauges, are commercially available with performance characteristics which meet the requirements of this application. Other devices can be envisaged which would achieve the same objective at lower cost. For example, a transducer employing the Hall Effect principle to detect changes in the deflection of a cantilevered beam with varying weight could be used for this purpose.

BRIEF DESCRIPTION OF THE DRAWINGS

In order that the invention may be more readily understood, reference will now be made to the accompanying drawings, in which.

DESCRIPTION OF THE PREFERRED EMBODIMENTS

Figure 1:
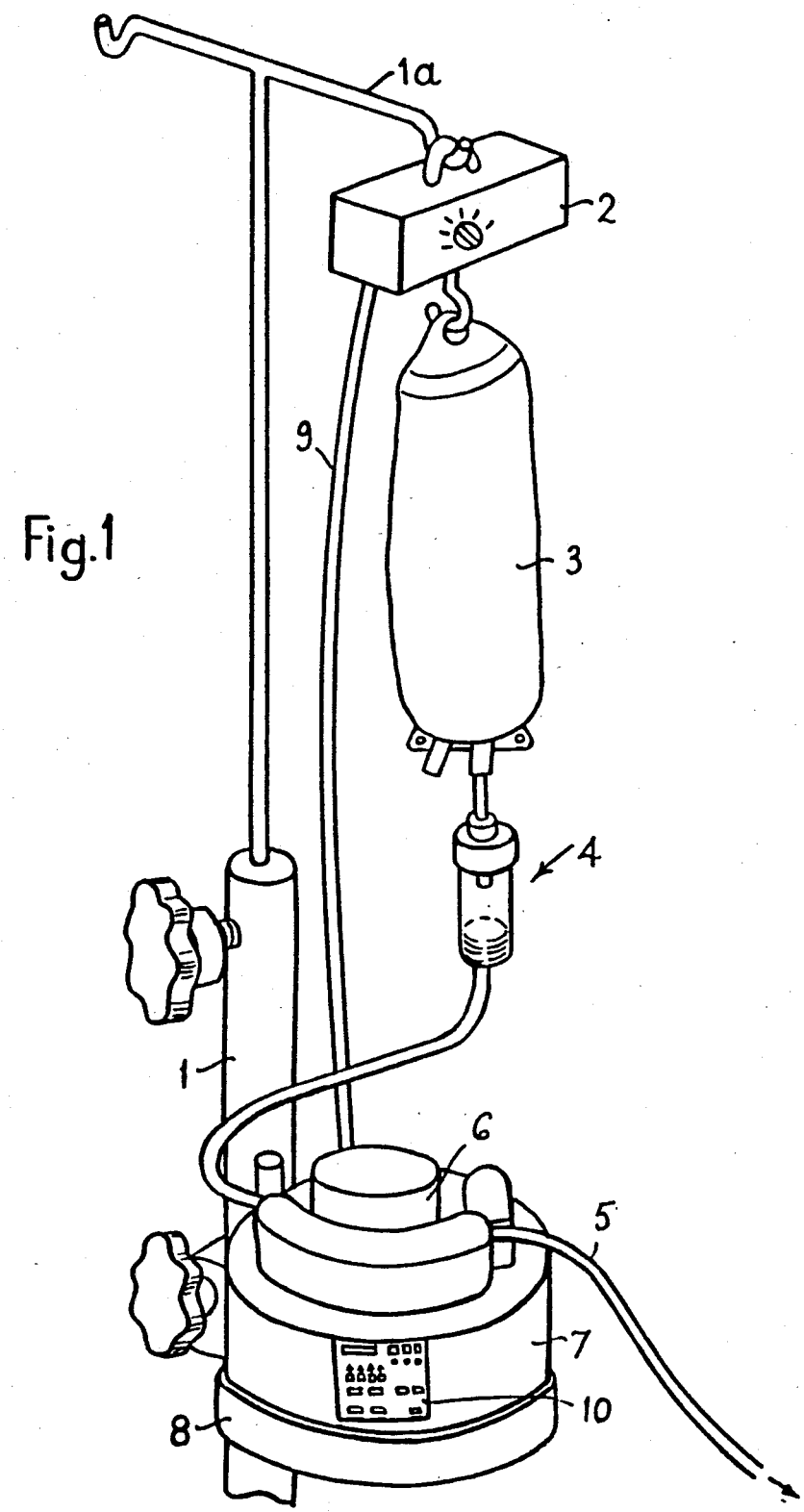
FIG. 1 illustrates an intravenous administration system incorporating a peristaltic pump and embodying the invention.

Referring to FIG. 1 of the drawings, the intravenous administration system is assembled on a standard I.V. pole 1 for administering an infusion to a patient. It comprises a weight sensing device 2 supported on one hook 1a of the I.V. pole, a standard fluid container or bag 3 suspended from the weight sensing device, and a standard administration set 4, via which fluid is dispensed from the container, and having its tube 5 threaded through the pumping head 6 of a rotary peristaltic pump 7 mounted on the I.V. pole by a suitable adjustable support clamp 8. The outlet end of the tube 5 is connected to an infusion needle or cannula (not shown) which is inserted into the patient at an appropriate injection site. The weight sensing device 2 is electrically connected to the pump 7 by means of a lead 9 and suitable plug and socket connections.

Prior to the commencement of infusion, the delivery rate to be used during the infusion is set or selected by means of the controls and display facility on the pump control panel 10, as will hereinafter be more fully described. At the start of the infusion and until information on actual delivery performance is fed back from the weight sensing device 2, this setting is processed within the electronic logic to run the pump 7 at a speed which, according to factory pre-setting, corresponds to the selected flow rate.

The weight sensing device 2 is arranged to monitor the actual delivery rate by detecting reduction in weight of the container 3 and providing digital signals identifying equal increments of weight reduction. As each increment is reached, a digital signal is produced indicating that a measured incremental weight and, hence, volume, of fluid has been dispensed since the preceding signal. This data, together with the time measured between each signal enables the control apparatus to determine the actual rate of delivery, compare it with the required delivery rate selected by the operator, and correct the speed of the pump drive accordingly. The function of the weight sensing device 2, therefore, is to provide data for repeated calibrations of the pump to ensure that actual performance corresponds to the required pumping or delivery rate.

Figure 2:
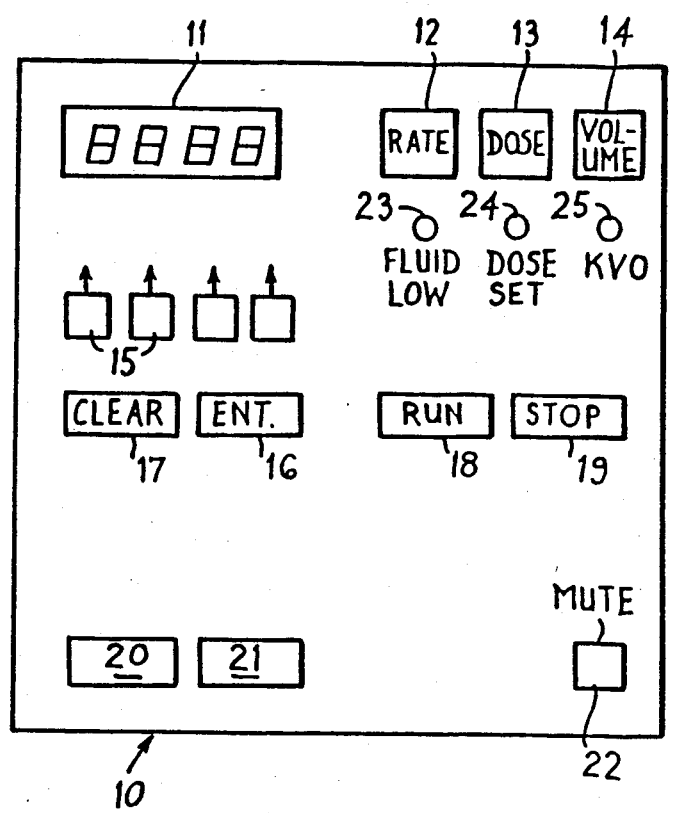
FIG. 2 is a fragmentary view of the control panel of the pump.

The control panel 10 is illustrated in more detail in FIG. 2 and includes a visual four digit display 11 which can be switched to show the delivery rate, the dose set or the volume dispensed by actuation of the "rate" key 12, the "dose" key 13 or the "volume" key 14, respectively. Digit set keys 15 enable each individual digit of the display 11 to be set to the required value and depending on which key 12 or 13 has previously been actuated, the display may be set to the required delivery rate or total dose. When either of these parameters has been set in the display it may be entered into the electronic control circuitry of the apparatus by actuating the enter key 16. In the event of an error, the display may be cleared by actuating the clear key 17. "Run" and "stop" keys 18,19 control starting and stopping of the pump and the control panel also includes other keys 20,21,22 for controlling other functions, such as, mains power and muting the audio alarm incorporated in the pump. Indicator lights 23,24,25 are installed for respectively providing warnings when the amount of fluid in the container 3 is low, when the system has been set to supply a specific dose, and when infusion is terminated but the pump is still revolving slowly so as to supply fluid to "keep vein open" (KVO). Preferably, the keys 12-22 are membrane switch devices. This type of switch is most suited for use on a pump because it enables the control panel to be sealed against the danger of fluid ingress.

Figure 3:
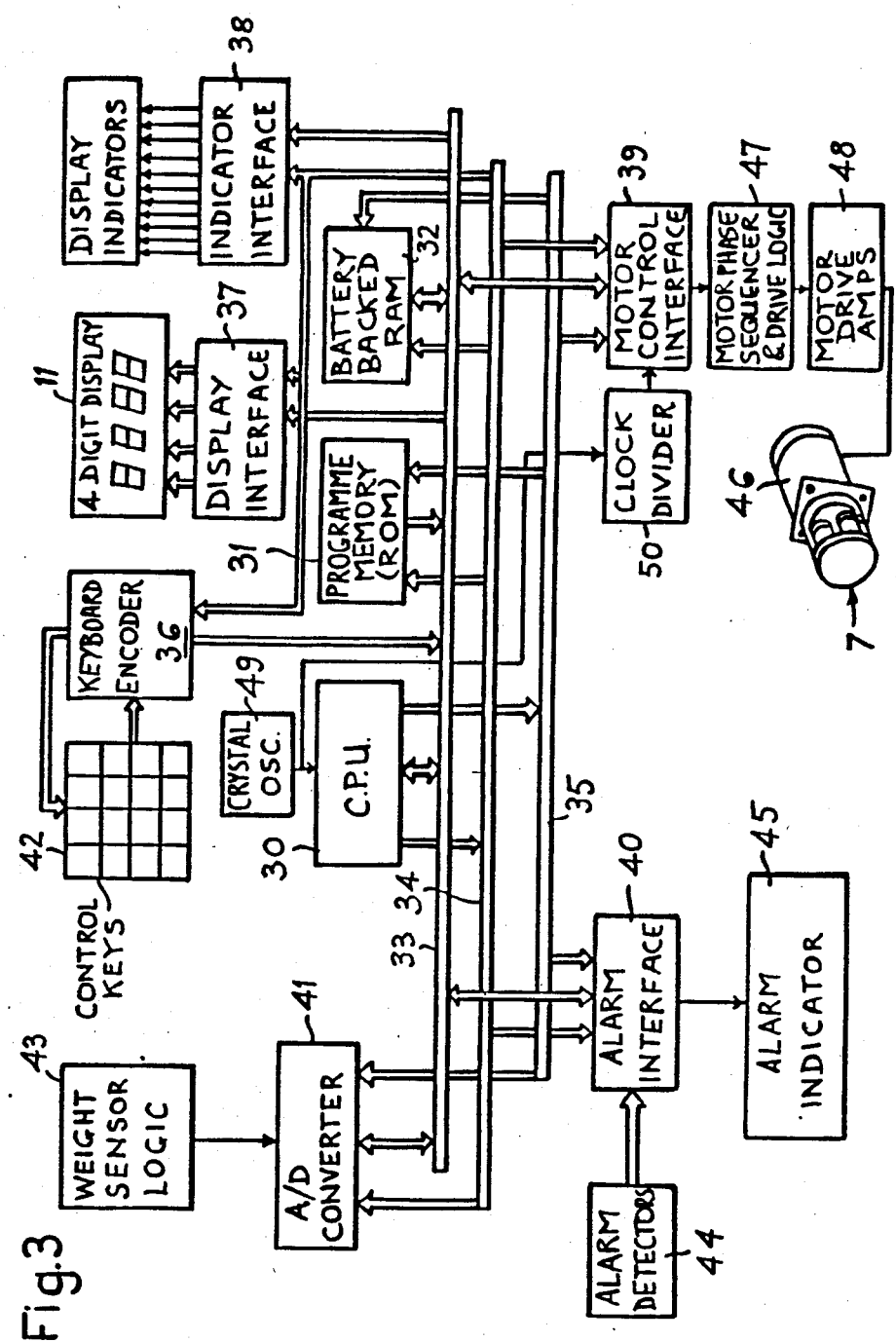
FIG. 3 is a block circuit diagram of the electronic flow control apparatus of the system.

Referring now to FIG. 3 which illustrates the control circuitry in more detail, this includes a central processing unit (CPU) 30, conveniently an 8-bit microprocessor, such as that marketed by R.C.A. Inc. under the model No. CDP 1806 ACE, a program memory (ROM) 31 storing the main operating program of the CPU, and a battery backed random access memory (RAM) 32.

The CPU and its associated memories 31,32 are interconnected by 8-bit data and address buses 33,34 and a control bus 35, which buses also interconnect these components with a keyboard encoder 36, a display interface 37, an indicator interface 38, a motor control interface 39, an alarm interface 40, and an analog-to-digital (A/D) converter 41 for supplying weight data.

The pump control keys 12-22 are diagrammatically illustrated in FIG. 3 at 42 and are connected to the keyboard encoder 36, which is responsive to actuation of the keys to produce coded data signals for onward transmission to the remainder of the control circuitry, via the data bus 33. These signals are coded in a manner which enables the CPU to recognise the control key which has been activated.

The weight sensing device 2 comprises weight sensor logic 43 for producing signals identifying the gross weight of the container or bag 3 and its contents and the A/D converter 41 for supplying corresponding digital weight signals via the data bus 33 to the CPU 30.

The alarm interface 40 is disposed between alarm detectors 44 for sensing certain dangerous or undesirable conditions or malfunctions of the pump and an audible alarm indicator 45.

The peristaltic pump 7, which is schematically illustrated in FIG. 3, is driven by a stepping motor 46. The mechanical construction of the peristaltic pump may be conventional and will not be described in detail as it does not, itself, form part of the present invention. The stepping motor 46 may, for example, be a four phase motor having a 1.8° step, that is, 200 steps per revolution. Trains of drive pulses are supplied to the motor 46 via the motor control interface 39 and conventional phase sequencer and logic drive circuitry 47 and drive amplifiers 48. A quartz crystal oscillator 49, for example, rated at approximately 2.4 mHz, is connected to supply timing pulses to the CPU 30 and also, via a clock divider 50 to the stepping motor circuitry. The clock divider feeds pulses at a constant rate to a 16-bit binary presettable downcounter incorporated in the control interface 39 and this downcounter is connected to supply drive pulses to the phase sequencer and drive logic 47 of the stepping motor at the rate of one drive pulse each time the downcounter is restored to zero by the train of pulses supplied by the clock divider 50. The downcounter is controlled by the CPU and serves as a variable pulse divider for producing motor drive pulse trains at different repetition rates for regulating the speed of rotation of the stepping motor.

The electronic logic of the pump is arranged so that all settings of the pump during previous use are restored to zero when the power supply is switched-off. Hence, all settings are at zero when the pump is switched-on and the display 11 is zeroised. In this condition the display 11 may be arranged to flash so as to indicate that digit set keys 15 have not yet been set for a running condition. It is also possible to introduce an automatic test procedure when first switching-on to assure the operator that all display segments are working and the alarm functions.

The delivery rate required (ml/hr) is set by the operator touching the "rate" key 12 and adjusting the display 11, with the aid of the set keys 15, to show the required setting. Actuation of any one of the set keys produces signals within the encoder 36 which, under the control of the CPU, are supplied directly, via the data bus 33 and the display interface 37, to the display logic 11 and cause the corresponding illuminated digit appearing in the display to index sequentially from zero to nine in response to each actuation of the associated key 15. Having set the required delivery rate in the display, this is entered into the control circuitry by actuating the "enter" key 16, whereupon the CPU addresses the display interface via its address logic and data corresponding to the digital setting of the display is loaded onto the data bus 33 for storage at the appropriate address in the RAM 32.

Any attempt to run the pump before the rate setting is made and entered will call an alarm condition and prevent the pump from starting.

If it is required to deliver a predetermined dose (mls), the "dose" key 13 is actuated and the dose is set in the display 11 and entered in the appropriate address in the RAM 32 in a similar manner to the delivery rate. When a dose is set, the pump automatically stops upon completion of the delivery of the dose or assumes a KVO mode, whereupon the indicator light 25 is illuminated. During running of the pump, the electronic circuitry is arranged to hold the selected delivery rate on display, but at any time either of the keys 13,14 may be actuated in order momentarily to display the set dose or instantaneous volume delivered.

When the control circuitry has been set to a selected delivery rate and dose, if required, the pump is ready to start the infusion. Preparation of the bag and administration set 4 is carried out similarly to a gravity infusion and the patency of the injection site may also be checked in the normal manner. With the administration set primed and ready for infusion, it may readily be loaded into the pump head 6 and infusion can be commenced by actuation of the "run" key 18.

Actuation of the "run" key 18 causes the encoder 36 to produce a coded signal which instructs the CPU 30 to address the sub-routine in its programme memory 31 which corresponds to that signal and the appropriate instructions issuing from this routine are loaded onto the data bus for onward transmission to the point of execution. The CPU controls acceptance of these instructions by the appropriate elements of the control circuit through its address logic. Preliminary stages in the sub-routine cause the CPU to address the various interfaces in the system to establish that the pump is not already running, that an alarm condition is not signalled, that a delivery rate has been set on the control panel, etc. When the pre-programmed system of priorities indicates the readiness of the CPU to act on the "run" instruction and the start up sequence can commence, the CPU issues instructions to the display interface 37 to hold the selected delivery rate on continuous visual display and accesses the selected delivery rate data from the RAM 32.

From the selected rate data, the CPU determines the speed at which the motor should rotate in order to deliver infusion fluid at the selected rate by reference to "look up" tables in its program memory 31. These tables supply the relationship between the selected rate data and the corresponding pump motor speed in the form of an hexadecimal reference number. This reference number which pertains to the required motor speed, is processed to produce control data for transmission to the motor control interface 39 and initial setting of the downcounter to supply a train of drive pulses at the pulse rate nominally required to drive the motor at the selected pumping rate.

In order to improve the accuracy of the initial setting, the CPU 30 is arranged to store, in the RAM 32, a factor which is computed from delivery rate information derived from the preceding dispensing operation, if any, and which is used to modify the reference number fetched from the program memory with a view to providing a more accurate nominal speed setting of the motor in relation to the selected delivery rate. The achievement of a more accurate setting by this technique assumes that, in a particular inventory, the administration sets will generally be of the same manufacture and have similar pumping characteristics.

Hence, upon commencement of infusion, the motor 46 is arranged to run at a predetermined speed which nominally corresponds to the delivery rate selected by the operator, subject to variations in the pumping performance of the tubing 5 used from that assumed during predetermination of the reference numbers or from that used during the preceding dispensing operation.

The signals supplied by the weight sensing device 2 are processed with respect to time by the CPU 30 to produce data identifying the actual fluid delivery rate and the CPU then compares this actual delivery rate data with the selected rate data and regulates the motor sped, when the actual delivery rate does not correspond with the selected delivery rate, in order to eliminate the error. As infusion progresses, analog data from the resistances of the strain gauge bridge circuit which form the weighing device are produced continually by the weight sensor logic 43. The data is amplified and converted to digital form by the A/D converter 41. The latter is continually monitored by the CPU 30 and, in the initial period after start-up, the CPU determines, under the control of the program stored in the program memory 31, when sufficient weight information has been supplied by the weight sensing device to enable its comparator logic to assume control of the motor speed. The converter 41 is accessed by the CPU and each time the latter detects a change in the least significant digit in the digital signal identifying the weight, the CPU instructs the converter to load the weight signal onto the data bus 33 for transmission to the CPU. The CPU processes this weight signal and from the time interval between each change in the least significant digit, which represents a known increment of weight, computes the actual delivery rate being achieved by the pump. A comparison between the actual delivery rate and the selected rate is then made by the CPU and the CPU supplies a signal to the motor control interface 39 to adjust the motor speed so as to conform the actual delivery rate to the selected rate. In order to vary the motor speed, the CPU supplies signals to the motor control interface 39 which adjust the setting of the downcounter in that interface and, hence, the repetition rate of the motor drive pulses. The CPU continuously monitors the balance between the actual and selected delivery rates to ensure that correspondence is maintained. Any requirement to set a specific gravity or density of the infused fluid for co-relation between weight change and volume change is accommodated within the CPU.

From the above it will be seen that the pump 7 is initially arranged to run at a predetermined set speed corresponding to the delivery rate selected by the operator. Upon receipt of the first acceptable signal from the weight sensing device 2 indicating that a discrete volume has been delivered, the CPU 30 determines the actual or true volumetric delivery rate and, when this does not correspond with the selected rate, corrects the speed of the motor in order to eliminate the error. Simultaneously, the total volume stored in the RAM 32 is updated to correspond with actual volume dispensed. At the next increment of weight, the process is repeated and similarly thereafter for each increment throughout the infusion to maintain close control over delivery. When determining the actual delivery rate at the end of each increment, the total volume delivered and the total time taken since the start of an infusion is used in order to avoid any progressive errors which might otherwise occur from measuring each increment in isolation.

The frequency of the incremental weight signals is determined by the number of resolution "bits" available in the A/D converter 41 and a suitable selection of this component is made to give the minimum number of bits, for reasons of cost, whilst maintaining adequate control over the system to ensure the required accuracy. The electronic logic of this part of the control system may be "geared" whereby the number of bits available on the A/D converter may be spread evenly over the total volume of fluid to be infused. This enables more frequent control to be exercised over infusions of small total volume where a greater degree of volumetric accuracy is required. The conversion of changes in weight to determine volume dispensed is, of course, dependent on the density of the infused liquid and the CPU includes logic providing a preset density factor accommodating the normal range of fluids used for infusions.

The control circuitry is arranged to function within certain limits between actual and selected delivery. If the CPU calls for corrective action, in terms of motor speed, which varies from the original condition by much more than would be expected for normal variations in the pumping performance of the tube 5, an alarm condition is called and the pump stops. The circuitry will not therefore accept major changes in delivery rate which might be caused, for example, by an occlusion of the delivery tube or excessive back pressure.

The CPU logic is designed to disregard transient signals from the weight sensing device resulting from jogging or movement of the system, such as whilst a patient is in transit. During the occurence of such transient signals, the CPU instructs the motor 46 to continue to function at the condition applying immediately prior to such occurrence. When the transient signals cease, the system reverts to its normal operating mode making any necessary corrections for deviation between actual and selected delivery which may have taken place during the movement period.

The dose facility may be used on multidispenser infusions to signal when changing of the container 3 is required. If a limiting volume is set to ensure that infusion is interrupted before the fluid container is exhausted, the situation can be avoided whereby the liquid level has fallen in the administration system to a point at which disconnection from the cannula is necessary to purge out any air before continuing with the infusion.

Provision is made within the operating program for changing the selected delivery rate or dose by simple manipulation of the controls at any time during infusion. This may be achieved by stopping the pump, actuating the "clear" key 17 in conjunction with the "rate" and/or "dose" keys 13,14 to clear the set rate and/or dose and re-setting the display to the fresh value or values required, as previously described. Additionally, the delivering rate may be changed whilst infusion is in progress by using the same procedure but without stopping the pump. Both the fluid container 3 and administration set 4 may be changed at any time without affecting the pump settings or the volumetric count of fluid dispensed up to that time.

The various safety alarms built into the system originate either as a result of check processes within the CPU 30, itself, for example, excessive divergence between actual and selected delivery rates, or by means of external detectors, for example, an air bubble sensor scanning the tube 5, pump head latch open, fluid low battery low, etc. The latter causes are routed to the alarm interface 40 and then to the CPU followed sequential address of the interface by the CPU. Upon acceptance of an alarm condition, the CPU activates the alarm indicator 45, via the alarm interface 40, stops the motor, or operates it in a KVO mode, and causes an alarm reference number to flash on the digital display 11 by means of instructions fed through the display interface 37.

The above described operating procedures of the microprocessor controlled electronic apparatus of the system are illustrated in the Flow Charts attached hereto as Annexes I–VII.

We claim:

1. A process of administering fluid to a patient and maintaining the actual volumetric delivery rate of said fluid in substantial conformity with a selected volumetric delivery rate throughout the administration procedure, comprising the steps of:

engaging an administration set, connected to a fluid container, with peristaltic pump means for delivering a flow of said fluid from said container and through said administration set, said pump means being driven by electrical drive motor means, actuating selected means to select a required volumetric delivery rate for said fluid and producing a signal identifying said selected delivery rate, utilising processing means to process said selected delivery rate signal and produce a control signal for said drive motor means corresponding to the speed thereof nominally required to drive said pump means at said selected delivery rate, said control signal being produced by accessing a routine of said processing means providing the relationship between selectable delivery rates and speeds of said drive motor means nominally required to produce said selectable delivery rates, initiating administration and operating said drive motor means at the speed established by said control signal, thereby to control the initial fluid delivery rate of said pump means, monitoring the weight of said fluid container and its contents with weight sensing means and producing weight signals corresponding to the loss in weight as said fluid is dispensed from said container, utilising said processing means to process said weight signals with respect to time and specific gravity of said fluid and produce data identifying the actual volumetric delivery rate of said fluid, comparing said selected delivery rate signal with said actual delivery rate data to produce a further control signal for said drive motor means corresponding to the operating speed of said drive motor means required to conform said actual delivery rate to said selected delivery rate, and subsequently utilising said further control signal to control said operating speed of said drive motor means and, hence, the delivery rate produced by said pump means after an initial start-up period determined by said processing means.

2. The process of claim 1, including the step of deriving a factor pertaining to fluid delivery rate from delivery rate data produced during a preceding administration procedure, and utilising said factor to modify said control signal produced by accessing said routine to provide for more accurate initial setting of said drive motor means.

3. Flow control apparatus for controlling the administration of fluid to a patient so as to maintain the actual volumetric delivery rate of said fluid in substantial conformity with a selected volumetric delivery rate throughout the administration procedure, said fluid being delivered to the patient through an administration set connected to a container for said fluid, comprising in combination:

peristaltic pump means for cooperating with said administration set and pumping said fluid therethrough, said pump means being driven by electrical drive motor means, regulating means for controlling the operating speed of said drive motor means, selection means for selecting a required volumetric delivery rate for said fluid and producing a signal identifying said selected rate, data processing means for processing said selected delivery rate signal and producing a control signal for said regulating means corresponding to the operating speed of said drive motor means nominally required to drive said peristaltic pump means at said selected delivery rate, said processing means utilising said control signal, upon initiation of said administration procedure, to set said regulating means and, hence, control the operating speed of said drive motor means and the delivery rate, whereby said actual delivery rate is controlled from the start of said administration procedure, and a weight sensing device for monitoring the weight of said fluid container and its contents and producing weight signals corresponding to the loss in weight as said fluid is pumped from said container, said processing means being adapted to process said weight signals with respect to time and specific gravity of said fluid and produce data identifying the actual volumetric delivery rate, said processing means being further adapted to compare said actual delivery rate data with said selected delivery rate signal and produce a further control signal for said regulating means corresponding to the operating speed of said drive motor means required to conform said actual delivery rate to said selected delivery rate, and said processing means being programmed to determine when sufficient weight data has been assimilated by said processing means and thereupon to utilise said further control signal to set said regulating means, whereby to maintain said actual delivery rate in substantial conformity with said selected rate.

4. The apparatus of claim 3, wherein said data processing means is arranged to fetch a weight signal from said weight sensing device in response to a predetermined increment of weight change, means is provided for supplying time signals, and said processing means computes said actual delivery rate data in response to sensing each predetermined increment of weight change, and wherein said data processing means is adapted to compute said actual delivery rate having regard to the total quantity of fluid delivered and the total time elapsed since initiation of said dispensing operation.

5. The apparatus of claim 3, wherein said selection means includes video display means for displaying said selected delivery rate, said selection means being selectively operable also to display total actual delivery data stored in said data processing means, and wherein said selection means is operable to set the total quantity of fluid to be dispensed during a dispensing operation and produce a total quantity signal, and said data processing means is adapted to store said total quantity signal and actuate said regulating means to stop delivery when the actual quantity of fluid delivered corresponds to said selected quantity.

6. The apparatus of claim 3, wherein said drive motor means for said peristaltic pump means comprises a stepping motor, and said regulating means includes a counter adjustable in response to said control signals supplied by said processing means to produce motor drive pulses at varying repetition rates, whereby to control the operating speed of said stepping motor.

7. The apparatus of claim 6, including means for supplying a train of operating pulses to said regulating means at a constant repetition rate, said regulating means including a downcounter arranged to be zeroised by said pulses, said downcounter being successively settable to predetermined counts in response to said control signals supplied by said processing means and producing a drive pulse each time it is zeroised by said train of operating pulses.

* * * * *